(12) United States Patent
Furrer et al.

(10) Patent No.: US 9,381,072 B2
(45) Date of Patent: Jul. 5, 2016

(54) ORTHOGNATHIC IMPLANT AND METHODS OF USE

(71) Applicant: DePuy Synthes Products, Inc., Raynham, MA (US)

(72) Inventors: Andre Furrer, Zuchwil (CH); Timo Zillig, Moehlin (CH); Marc Christian Metzger, Kirchzarten (DE)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/731,587

(22) Filed: Jun. 5, 2015

(65) Prior Publication Data
US 2015/0265378 A1    Sep. 24, 2015

Related U.S. Application Data

(62) Division of application No. 12/770,088, filed on Apr. 29, 2010, now Pat. No. 9,066,733.

(51) Int. Cl.
*A61C 8/00* (2006.01)
*G06F 19/12* (2011.01)
*A61B 17/17* (2006.01)
(Continued)

(52) U.S. Cl.
CPC .............. *A61C 8/0031* (2013.01); *A61B 6/14* (2013.01); *A61B 17/151* (2013.01); *A61B 17/17* (2013.01); *A61B 17/1739* (2013.01); *A61B 17/80* (2013.01); *A61B 17/8061* (2013.01); *A61B 17/8071* (2013.01); *A61B 17/8085* (2013.01); *A61C 8/0089* (2013.01); *A61C 9/004* (2013.01); *A61C 13/0004* (2013.01); *G06F 19/12* (2013.01); *A61B 17/176* (2013.01); *A61B 17/1728* (2013.01); *A61B 17/808* (2013.01); *A61B 2017/00526* (2013.01); *G05B 19/182* (2013.01); *G05B 2219/49023* (2013.01)

(58) Field of Classification Search
CPC .. A61C 9/004; A61C 8/0089; A61C 13/0004; A61B 6/14; G06F 19/12; G05B 2219/49023
See application file for complete search history.

(56) References Cited

U.S. PATENT DOCUMENTS 3,955,567 A    5/1976  Richmond et al.
4,484,570 A   11/1984  Sutter et al.
(Continued)

FOREIGN PATENT DOCUMENTS

CN    21469764 Y    11/1993
CN    2668063 Y     1/2005
(Continued)

OTHER PUBLICATIONS

U.S. Appl. No. 13/078,250, filed Apr. 1, 2011, André Furrer.
(Continued)

*Primary Examiner* — Christian Sevilla
(74) *Attorney, Agent, or Firm* — Baker & Hostetler LLP

(57) ABSTRACT

An implant for use in orthognathic surgery of a maxilla may include a longitudinal plate member and a plurality of pre-shaped fingers extending from an upper edge of the plate member. The longitudinal plate member is pre-shaped to correspond to the pre-operative shape of the maxilla; and the fingers are pre-shaped to correspond to the shape of the maxilla. The fingers may be pre-shaped to correspond to either the pre-operative shape or the post-operative shape of the maxilla.

17 Claims, 11 Drawing Sheets

(51) Int. Cl.

| | | |
|---|---|---|
| *A61B 17/80* | (2006.01) | |
| *A61B 17/15* | (2006.01) | |
| *A61B 6/14* | (2006.01) | |
| *A61C 9/00* | (2006.01) | |
| *A61C 13/00* | (2006.01) | |
| *A61B 17/00* | (2006.01) | |
| *G05B 19/18* | (2006.01) | |

(56) References Cited

U.S. PATENT DOCUMENTS

| | | | |
|---|---|---|---|
| 4,575,805 A | 3/1986 | Moermann et al. | |
| 4,966,599 A | 10/1990 | Pollock | |
| 4,976,737 A | 12/1990 | Leake | |
| 5,052,930 A | 10/1991 | Lodde et al. | |
| 5,306,150 A | 4/1994 | Gittleman | |
| 5,364,396 A | 11/1994 | Robinson et al. | |
| 5,373,860 A * | 12/1994 | Catone | A61B 17/8863 128/897 |
| 5,452,407 A | 9/1995 | Crook | |
| 5,622,493 A | 4/1997 | Razdolsky et al. | |
| 5,690,631 A | 11/1997 | Duncan et al. | |
| 5,769,637 A | 6/1998 | Morgan | |
| 5,836,948 A | 11/1998 | Zucherman et al. | |
| 5,885,283 A | 3/1999 | Gittleman | |
| 5,895,387 A | 4/1999 | Guerrero et al. | |
| 6,053,919 A | 4/2000 | Talos et al. | |
| 6,221,075 B1 | 4/2001 | Tormala et al. | |
| 6,254,639 B1 | 7/2001 | Peckitt | |
| 6,350,265 B1 | 2/2002 | Blaustein et al. | |
| 6,712,851 B1 | 3/2004 | Lemperle et al. | |
| 6,863,694 B1 | 3/2005 | Boyce et al. | |
| 6,932,842 B1 | 8/2005 | Litschko et al. | |
| 6,972,020 B1 | 12/2005 | Grayson et al. | |
| 6,978,188 B1 | 12/2005 | Christensen | |
| 7,172,422 B1 | 2/2007 | Essiger | |
| 8,177,822 B2 * | 5/2012 | Medoff | A61B 17/809 606/297 |
| 9,066,733 B2 | 6/2015 | Furrer et al. | |
| 2002/0062127 A1 | 5/2002 | Schumacher et al. | |
| 2002/0116002 A1 | 8/2002 | Sellers | |
| 2002/0128654 A1 | 9/2002 | Steger et al. | |
| 2003/0105463 A1 | 6/2003 | Wolgen | |
| 2003/0139748 A1 | 7/2003 | Koseki | |
| 2004/0138591 A1 | 7/2004 | Iseki et al. | |
| 2004/0166469 A1 | 8/2004 | Tremont | |
| 2005/0039759 A1 | 2/2005 | Mauro | |
| 2005/0059864 A1 | 3/2005 | Fromovich et al. | |
| 2005/0182408 A1 | 8/2005 | Pfefferle et al. | |
| 2005/0192675 A1 | 9/2005 | Robinson | |
| 2005/0256526 A1 | 11/2005 | Johnston | |
| 2006/0116682 A1 | 6/2006 | Longo | |
| 2006/0235408 A1 * | 10/2006 | Wang | A61B 17/663 606/281 |
| 2007/0043370 A1 | 2/2007 | Ueda et al. | |
| 2007/0118243 A1 | 5/2007 | Schroeder et al. | |
| 2008/0081315 A1 | 4/2008 | Kim et al. | |
| 2008/0195240 A1 | 8/2008 | Martin et al. | |
| 2009/0131944 A1 | 5/2009 | Noon et al. | |
| 2011/0301609 A1 | 12/2011 | Longepied | |
| 2012/0029574 A1 | 2/2012 | Furrer et al. | |
| 2012/0150243 A9 * | 6/2012 | Crawford | G06F 19/3437 606/86 R |
| 2012/0289965 A1 * | 11/2012 | Gelaude | A61B 17/15 606/87 |

FOREIGN PATENT DOCUMENTS

| | | |
|---|---|---|
| CN | 2902227 Y | 5/2007 |
| CN | 201171708 Y | 12/2008 |
| CN | 201341974 Y | 11/2009 |
| CN | 101637413 A | 2/2010 |
| DE | 4018273 | 1/1991 |
| DE | 91 15 341 | 2/1992 |
| DE | 19629011 | 1/1998 |
| DE | 102006043204 | 3/2008 |
| DE | 102008017619 | 4/2009 |
| EP | 0 290 138 | 11/1988 |
| EP | 0 566 255 | 10/1993 |
| EP | 0 748 616 | 12/1996 |
| EP | 0 890 345 | 1/1999 |
| EP | 1 088 520 | 4/2001 |
| EP | 1 468 656 | 10/2004 |
| EP | 1 502 556 | 2/2005 |
| EP | 1654994 A1 | 5/2006 |
| EP | 2 030 596 | 3/2009 |
| EP | 2 179 701 | 4/2010 |
| GB | 2324470 A | 10/1998 |
| JP | 09215699 | 8/1997 |
| JP | 10043203 | 2/1998 |
| JP | 11-508464 | 7/1999 |
| JP | 2005028046 | 2/2005 |
| WO | WO 91/14404 | 10/1991 |
| WO | WO 97/20512 | 6/1997 |
| WO | WO 99/44529 | 9/1999 |
| WO | WO 01/34044 | 5/2001 |
| WO | WO 01/78612 | 10/2001 |
| WO | WO 02/28298 | 4/2002 |
| WO | WO 2005/117760 | 12/2005 |
| WO | WO 2006/020245 | 2/2006 |
| WO | WO 2007/142743 | 12/2007 |
| WO | WO 2008/112074 A2 | 9/2008 |

OTHER PUBLICATIONS

International Patent Application No. PCT/US2010/032908: International Search Report dated Nov. 29, 2010, 7 pages.
International Patent Application No. PCT/US2011/030885: International Search Report dated Nov. 29, 2010, 7 pages.

* cited by examiner

ORTHOGNATHIC IMPLANT AND METHODS OF USE

CROSS REFERENCE TO RELATED APPLICATIONS

This application is a Divisional of U.S. application Ser. No. 12/770,088, filed on Apr. 29, 2010, the entire contents of which are expressly incorporated herein by reference thereto.

BACKGROUND

Orthognathic surgery is generally performed to correct conditions of the jaw and face related to structure, growth, sleep apnea, TMJ disorders or to correct orthodontic problems. For example, an individual who has a significantly receded upper jaw or an open bite might benefit from a maxillary osteotomy. In such a procedure, a surgeon makes cuts below both eye sockets to separate a segmented part of the maxilla from an intact portion of the maxilla. The entire segmented part, including the roof of the mouth and all upper teeth, can move as a single unit. The segmented part is then moved until the upper and bottom teeth fit together properly. Once the teeth are realigned, tiny screws and plates are used to fix the segmented part of the maxilla in its new position until natural bone healing takes place.

Some orthognathic surgeries affix multiple plates to the maxilla to hold the cut segmented part of the maxilla relative to the second intact part. As one could imagine, the adaptation and use of multiple plates make the procedure unnecessarily long and complicated.

Other plating systems require multiple disciplines such as surgeons, dentists, orthodontists, etc to complete the procedure. As a result there often times are misunderstandings between the disciplines. These and other disadvantages are attributed to such plating systems used in orthognathic surgeries.

Therefore, it may be desired to achieve a better and more accurate way of planning and performing orthognathic surgery.

SUMMARY

The disclosure generally relates to an improvement in implants used in orthognathic surgery, and in particular, patient specific plates for use in orthognathic surgery. However, the disclosed implants are not limited to this specific application.

In one embodiment, an implant for use in orthognathic surgery may include a plate member and a plurality of fingers extending out from the plate member. The plate member is pre-shaped to correspond to a pre-operative shape of a maxilla. The plate member includes at least one fixation aperture that extends through the plate member and is configured to receive a bone fixation element so as to secure the plate member to the maxilla. The fingers are pre-shaped to correspond to the shape of the maxilla.

In another embodiment an implant that is configured to join a first part of the maxilla to a second part of the maxilla after a segmentation procedure that separates the first part of the maxilla from the second part of the maxilla is disclosed. The implant includes a plate member and a holding structure that extends from the plate member. The plate member is pre-shaped, prior to the segmentation procedure, so as to correspond to an outer surface of the first part of the maxilla after the segmentation procedure. The plate member includes at least one aperture configured to receive a fixation element so as to secure the plate member to the first part of the maxilla. The holding structure is pre-shaped so as to correspond to the second part of the maxilla after the segmentation procedure.

In another embodiment, an osteotomy guiding implant for use in orthognathic surgery is disclosed. The osteotomy guiding implant may include a plate member and a plurality of fingers that extend from the plate member. The plate member and the fingers are pre-shaped to correspond to a pre-operative shape of a maxilla. Each finger defines an aperture, such that the apertures of the fingers are arranged to provide a template for pre-osteotomy drilling holes that define a cutting guide path on the maxilla so as to separate a segmented portion of the maxilla from an integral portion of the maxilla.

In another embodiment, the implant may include a plate member having a first portion, and a second portion separated by a bridge portion. The first and second portions each include at least one aperture configured to receive a fixation element so as to secure the plate member to bone. At least one finger extends from each of the first and second portions, wherein each finger includes at least one aperture configured to receive a fixation element so as to secure each finger to bone. After the plate member has been secured to bone, the bridge portion is removable to thereby separate the first portion of the plate member from the second portion of the plate member.

A method for correcting the shape of a maxilla, is also disclosed. Preferably a plurality of locations on the maxilla at which a plurality of holes are to be located is determined. A guiding implant is positioned on the maxilla such that guiding apertures of the guiding implant are arranged to align with the plurality of locations. Holes are then made in the maxilla using the guiding apertures of the guiding implant. Based on the location of the holes, an osteotomy is performed to separate the maxilla into at least a first part and a second part. Once the osteotomy is completed, a pre-shaped bone fixation implant is positioned on the maxilla and is arranged to hold the maxilla in a corrected shape. The bone fixation implant is pre-shaped to correspond to the post-operative shape of the maxilla. Once in place, the bone fixation implant is affixed to the maxilla using fixation elements.

A method of customizing a pre-shaped implant for use in orthognathic surgery of a maxilla is also disclosed. To customize the implant a pre-operative 3-D model of a patient's maxilla is first obtained in a computer whereby the first portion of the maxilla and the second portion of the maxilla define first relative position. The pre-operative 3-D model of the maxilla is then manipulated into a post-operative shape, whereby the first portion of the maxilla and the second portion of the maxilla define a second relative position that is different than the first relative position. Once in the desired position, a bone fixation implant is custom constructed to match the planned post-operative shape of the maxilla. The implant may include a longitudinal plate member and a plurality of fingers that extend from an upper edge of the plate member.

BRIEF DESCRIPTION OF THE DRAWINGS

The foregoing summary, as well as the following detailed description of example embodiments, are better understood when read in conjunction with the appended diagrammatic drawings. For the purpose of illustrating the invention, the drawings show embodiments that are presently preferred. The invention is not limited, however, to the specific instrumentalities disclosed in the drawings.

FIG. 5A is a front view of a skull, including a maxilla bone that is to be operated on;

DETAILED DESCRIPTION OF ILLUSTRATIVE EMBODIMENTS

Figure 1:
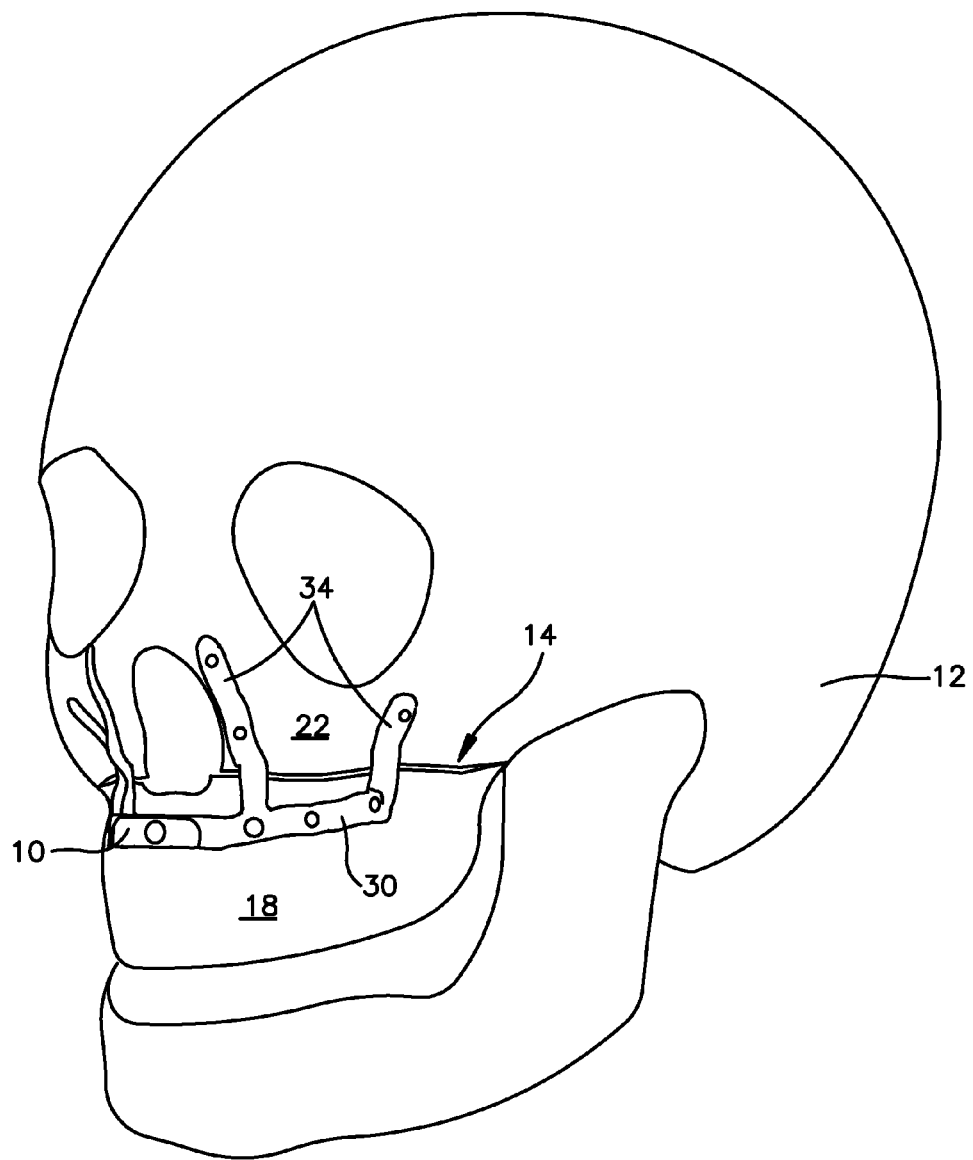
FIG. 1 is a perspective view of a skull with a bone fixation implant affixed to the maxilla.

Referring to FIG. 1 a bone fixation implant 10 to be used in orthognathic surgery is designed to be fixed to underlying bone such as a patient's skull 12, and in particular to a patient's maxilla 14 after the maxilla 14 has been separated into a first "segmented" part 18 and a second "integral" part 22 by a segmentation procedure, such as an osteotomy. The first part 18 of the maxilla 14 typically carries the upper teeth and is completely separated from the skull 12 after the osteotomy has been performed, while the second part 22 of the maxilla 14 remains intact with the skull 12. The bone fixation implant 10 is configured to attach to the first and second parts of the maxilla, and thereby support and hold the first part 18 of the maxilla relative to the second part 22 while osteogenesis occurs. The implant 10 is customized pre-operatively to minimize complications during surgery and time spent in the operating room by a patient.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases designate preferred positions and orientations in the human body to which reference is made and are not meant to be limiting. The terminology includes the above-listed words, derivatives thereof and words of similar import.

Referring to FIGS. 2A-2D, the implant 10 and various components of the implant are described herein extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. When the implant 10 is implanted onto a maxilla, such as the maxilla 14, the transverse direction T extends vertically generally along the superior-inferior (or caudal-cranial) direction, while the plane defined by the longitudinal direction L and lateral direction A extends horizontally, generally in the anatomical plane defined by the medial-lateral direction and the anterior-posterior direction. Accordingly, the directional terms "vertical" and "horizontal" are used to describe the implant 10 and its components as illustrated merely for the purposes of clarity and illustration.

As shown in FIGS. 2A-2D, the bone fixation implant 10 includes a longitudinal plate member 30 that is elongate and curved in the longitudinal direction L and a holding structure 34 that extends vertically from the longitudinal member 30. The longitudinal plate member 30 includes an upper edge 38, a bone engaging surface configured to lie substantially flush with the maxilla, and an outer surface opposed to the bone engaging surface. Therefore, the holding structure 34 extends up from the upper edge 38 of the longitudinal member 30. As shown in FIG. 1, the bone fixation implant 10 supports and holds the first part 18 of the maxilla relative to the second part 22 while osteogenesis occurs. The bone fixation implant 10 and components thereof, can be formed from a variety of biocompatible materials, such as cobalt chromium molybdenum (CoCrMo), titanium, and titanium alloys, stainless steel, ceramics, or polymers such as polyetheretherketone (PEEK), polyetherketoneketone (PEKK), and bioresorbable materials. A coating may be added or applied to the bone fixation implant 10 to improve physical or chemical properties or to provide medications. Examples of coatings include plasma-sprayed titanium coating or Hydroxyapatite.

Figure 2A:
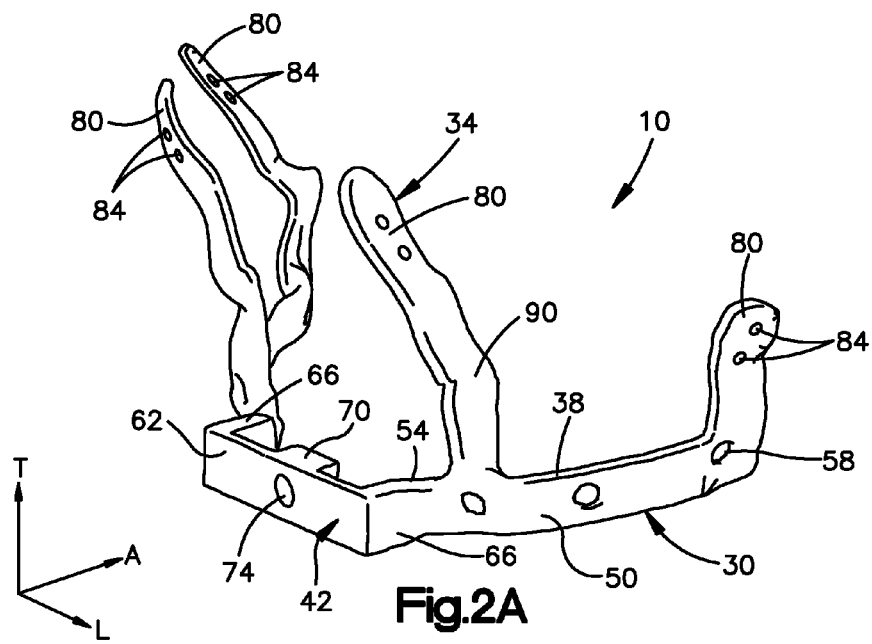
FIG. 2A is a perspective view of a bone fixation implant constructed in accordance with one embodiment.
Figure 2B:
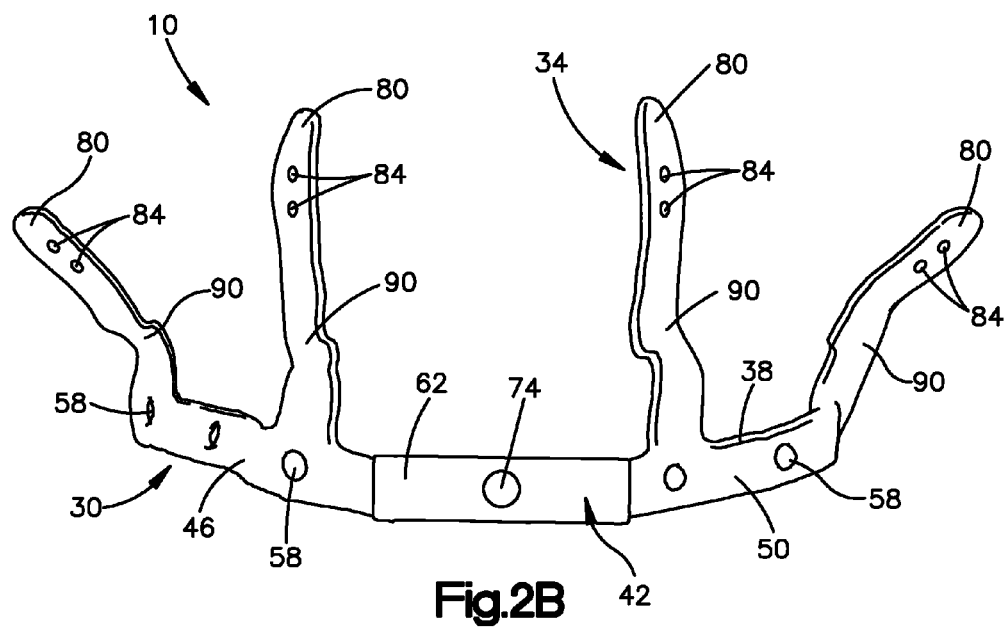
FIG. 2B is a front view of the bone fixation implant shown in FIG. 2A.
Figure 2C:
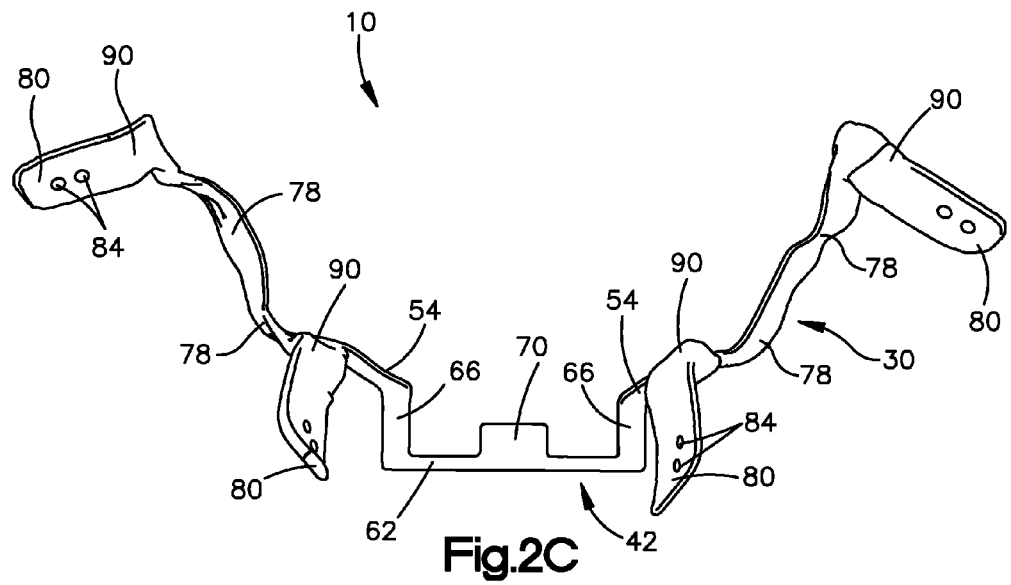
FIG. 2C is a top view of the bone fixation implant shown in FIG. 2A.
Figure 2D:
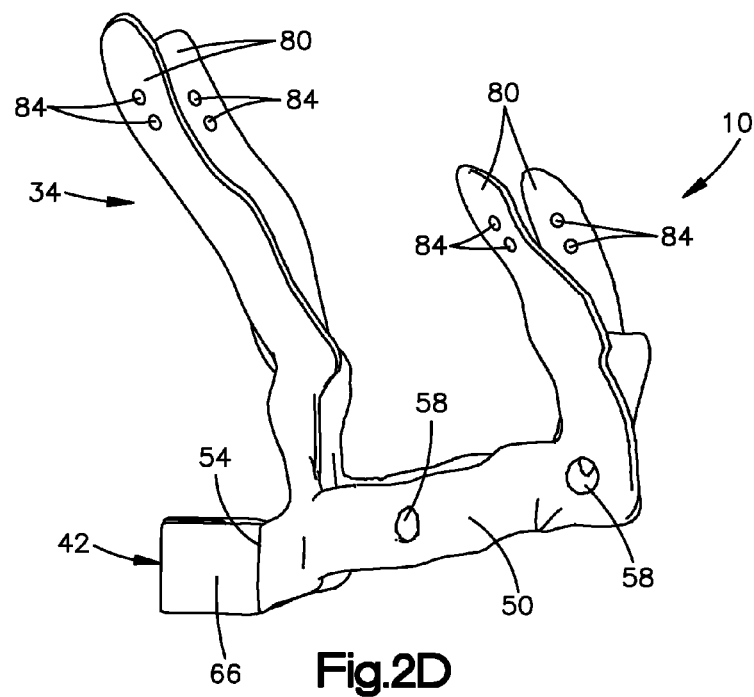
FIG. 2D is a left side view of the bone fixation implant shown in FIG. 2A.

As shown in FIGS. 1, and 2A-2D, the longitudinal member 30 is configured to be attached to the first part 18 of the maxilla 14. In general, the longitudinal member 30 includes a central bridge member 42 that separates the longitudinal member 30 into a first portion 46 and a second portion 50. The first and second portions 46, 50 extend from the bridge member 42 from respective junctions 54. As shown, the first portion 46 extends from the bridge member 42 in a first direction, while the second portion 50 extends from the bridge member 42 in a second direction that is generally opposite to the first direction. As best shown in FIG. 2C, the first portion 46 and the second portion 50 each curves in the lateral direction A as they extend longitudinally. Therefore, as best shown in FIG. 2C, the longitudinal member 30 is curved such that it forms generally a C-shaped structure. Furthermore, as best shown in FIGS. 2B and 2D, the first portion 46 and the second portion 50 each angle up in the transverse direction T as they extend longitudinally. The curvature and shape of the longitudinal member 30 generally correspond to the shape of the maxilla 14.

Additionally, the first and second portions 46, and 50 of the longitudinal member 30 include a plurality of fixation element receiving apertures/holes 58 that extend from the outer surface of the longitudinal member 30 and through to the bone engaging surface. Each hole 58 is configured to receive a fixation element, such as a screw. Though it should be understood that any fixation element will suffice. The implant 10 is configured to be fastened to the first part 18 of the maxilla 14 by inserting fixation elements through each hole 58 of the longitudinal member 30 and into the first part 18 of the maxilla 14.

The bridge member 42 of the longitudinal member 30 includes a plate 62 that is elongate in the longitudinal direction L, an extension 66 extending in the lateral direction A from each end of the plate 62, and a centrally located protrusion 70 that also extends laterally from an inner surface of the plate 62. The junctions 54 are located at the posterior ends of each extension 66. Thus, the first and second portions 46, 50 of the longitudinal member 30 each extend from a posterior end of a respective extension 66 of the bridge member 42. The bridge member 42 may be removed from the longitudinal member 30 at the junctions 54 once the implant 10 is secured to the maxilla 14. The junction points 54 may be weakened so that the bridge member 42 may be easily removed once the implant 10 is secured to the maxilla 14. For example, junctions 54 may be thinned, or perforated, or otherwise configured, so that the bridge member 42 may be removed by snapping the bridge member 42 away. It should be understood however that the bridge member 42 may be removed by cutting the junction points 54 with snips or pliers. Because the bridge member 42 is removable, the amount of the implant 10 left in the patient may be minimized.

As shown in FIG. 2B, the bridge member further includes a reference hole 74 that extends laterally through both the plate 62 and the protrusion 70 of the bridge member 42. The implant 10 may initially be fastened to the maxilla 14 by inserting a fixation element through the reference hole 74 and into the maxilla 14. The fixation element inserted into the reference hole 74 may temporarily affix the implant 10 to the maxilla 14 while a surgeon correctly aligns the implant 10 for complete fixation to the maxilla 14.

The longitudinal member 30 and in particular the first and second portions 46, 50, is pre-shaped to correspond to the post-operative shape of the first part 18 of the maxilla 14. In this regard the longitudinal member is pre-shaped prior to the segmentation procedure, so as to correspond to an outer surface of the first part of the maxilla after the segmentation procedure. While it is preferable that the member 30 is pre-shaped such that no manual bending is required prior to placement of the implant 10 onto the maxilla 14, the member 30 may be pre-shaped such that only minimal bending is required prior to placement of the implant 10 onto the maxilla 14 (e.g. bending that may take place when fastening the member 30 to the maxilla 14). As best shown in FIG. 2C, the first and second portions 46, 50 include several non-linear undulations 78 that correspond to particular surface portions of the first part 18 of the maxilla 14. It should be understood, however, that the shape of the first part 18 of the maxilla 14 may be unchanged between the pre-operative and post-operative shape of the maxilla 14. Therefore, the longitudinal member 30 may be pre-shaped to correspond to both the pre-operative shape and the post-operative shape of the first part 18 of the maxilla 14.

As shown in FIGS. 2A-2D, the holding structure 34 of the implant 10 includes at least one finger 80, such as a plurality of fingers 80 that extend up from the upper edge 38 of the longitudinal member 30. In accordance with the illustrative embodiment, two fingers 80 extend from each of the first and second portions 46, and 50 of the longitudinal member 30. However, it should be understood that any number of fingers 80 may extend up from the first and second portions 46, and 50. As shown, each finger 80 includes at least one fixation element receiving aperture or hole 84 configured to receive a fixation element, such as a screw, so as to affix the fingers 80 to the second part 22 of the maxilla 14. Though it should be understood any fixation element will suffice. While the embodiment illustrated shows each finger 80 having two holes 84, it should be understood, that each finger may have any number of holes, e.g. 1, 2, 3, 4, etc.

As best shown in FIG. 2B, the fingers 80 are spaced apart along the first and second portions 46, 50 of the longitudinal member 30 and extend substantially perpendicularly relative to the point on the portions 46, 50 from where they extend. That is, the longitudinal plate member 30 is non-linear and will define tangents at different points along its edge 38. Therefore, each finger 80 will extend perpendicular with respect to a tangent taken at the point on the edge 38 from which the finger 80 extends. Though it should be understood that the fingers 80 do not have to extend perpendicularly, and may extend at some angle relative to the longitudinal member 30. Preferably, each finger 80 extends from the longitudinal member 30 such that a fixation element hole 58 of the longitudinal member 30 is aligned with the point at which a respective finger 80 extends from the edge 38 of the longitudinal member 30, to further improve equal force distribution throughout the implant 10.

The holding structure 34 or fingers 80 are pre-shaped to correspond to the post-operative shape of the second part 22 of the maxilla 14, and extend from the first and second portions 46, 50, so as to provide a fixation member that corresponds to the shape and the relationship of the first parts of the maxilla. In this regard the fingers 80 are pre-shaped prior to the segmentation procedure, so as to correspond to an outer surface of the second part of the maxilla after the segmentation procedure. While it is preferable that the fingers 30 are pre-shaped such that no manual bending is required prior to placement of the implant 10 onto the maxilla 14, the fingers 80 may be pre-shaped such that only minimal bending is required prior to placement of the implant 10 onto the maxilla 14. Therefore, as best shown in FIG. 2C, the fingers 80 include several non-linear undulations 90 that correspond to particular surface portions of the second part 22 of the maxilla 14. Because the fingers 80 are pre-shaped, they will fit correctly only at the desired location of the maxilla 14 and provide a surgeon with positive assurance that they have achieved correct alignment and, therefore, a desired corrected shape.

Before the implant 10 is affixed to the maxilla, an osteotomy is performed to separate the maxilla 14 into the first part 18 and the second part 22. A temporary osteotomy guiding implant 110 may be affixed to the maxilla 14 before the osteotomy is performed on the maxilla 14 to create a guide for the surgeon. In particular, the osteotomy guiding plate 110 provides a template for a surgeon to follow while performing the osteotomy. For example, the osteotomy guiding implant 110 allows the surgeon to make guide holes in the maxilla to follow while performing the osteotomy. In this way, the osteotomy guiding implant acts as a drill guiding implant. The osteotomy guiding implant also provides a template for the surgeon to follow while implanting the bone implant 10.

The osteotomy guiding implant 110 is also customized pre-operatively to minimize complications during surgery and time spent in the operating room by a patient.

As shown in FIGS. 3A-3D, the osteotomy guiding implant 110 includes a longitudinal plate member 130 that is elongate and curved in the longitudinal direction L, and a template portion 132 that includes a plurality of fingers/protrusions 134 that extend vertically in the transverse direction T from the longitudinal member 130. Like the implant 10, the osteotomy guiding implant 110 includes an upper edge 138, a bone engaging surface configured to lie substantially flush with the maxilla, and an outer surface opposed to the bone engaging surface. The osteotomy guiding implant 110 and components thereof, can be formed from a variety of biocompatible materials, such as cobalt chromium molybdenum (CoCrMo), titanium, and titanium alloys, stainless steel, ceramics, or polymers such as polyetheretherketone (PEEK), polyetherketoneketone (PEKK), and bioresorbable materials. A coating may be added or applied to the osteotomy guiding implant 110 to improve physical or chemical properties or to provide medications. Examples of coatings include plasma-sprayed titanium coating or Hydroxyapatite.

Figure 3A:
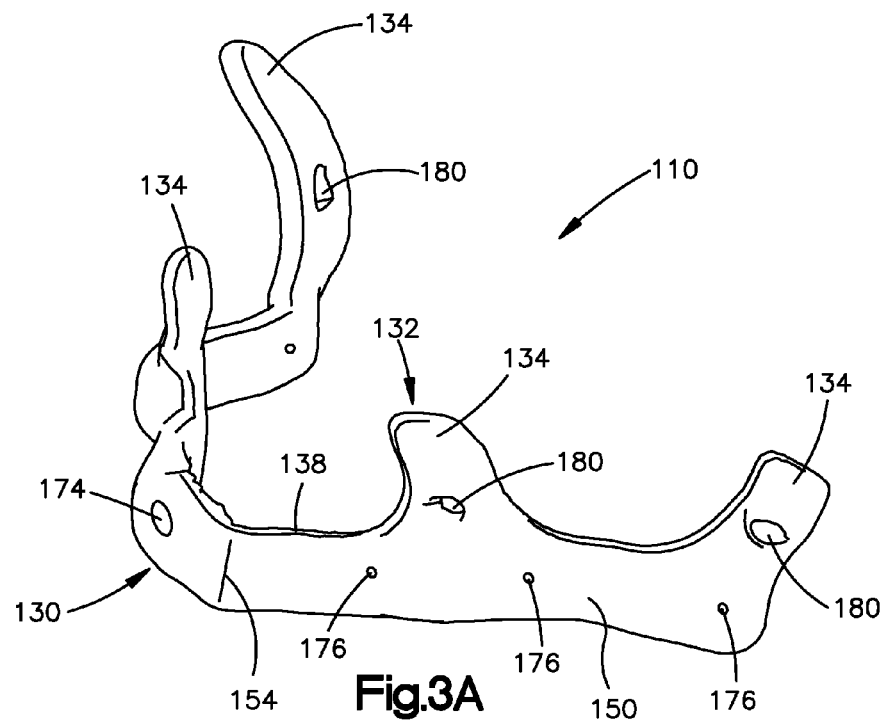
FIG. 3A is a perspective view of an osteotomy guiding implant constructed in accordance with one embodiment.
Figure 3B:
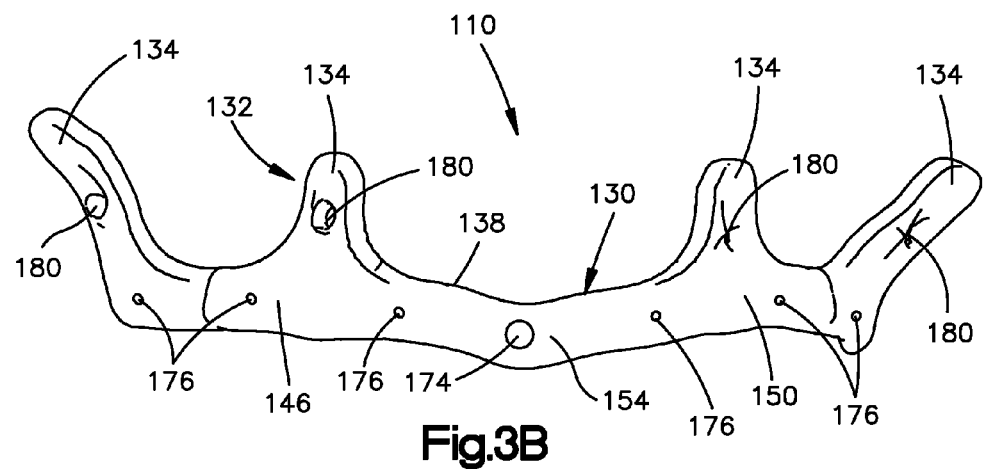
FIG. 3B is a front view of the osteotomy guiding implant shown in FIG. 3A.
Figure 3C:
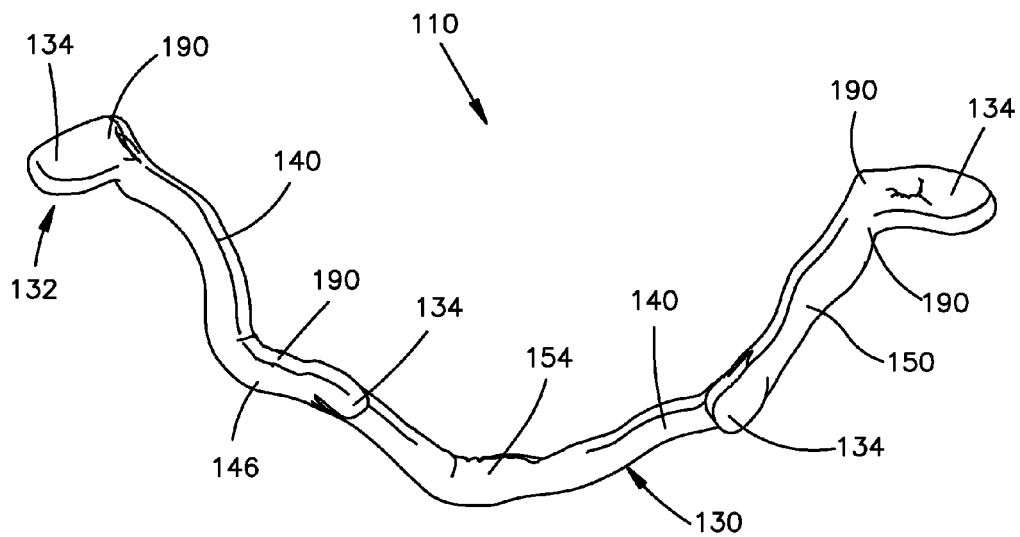
FIG. 3C is a top view of the osteotomy guiding implant shown in FIG. 3A.
Figure 3D:
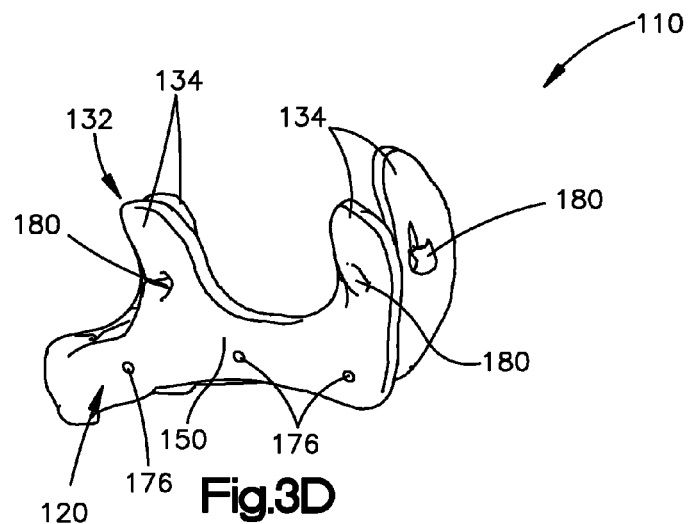
FIG. 3D is a left side view of the osteotomy guiding implant shown in FIG. 3A.

As best shown in FIG. 3C, the longitudinal plate member 130 includes a first portion 146 and a second portion 150 that extend in opposite directions from a central juncture 154. Each portion 146 and 150 curves in the lateral direction A as it extends longitudinally. Therefore, as shown in FIG. 3C, the longitudinal member 130 is curved such that it forms generally a C-shaped structure similar to the bone fixation implant 10. Furthermore, as best shown in FIGS. 3B and 3D, the first portion 146 and the second portion 150 each angle up in the transverse direction T as they extend longitudinally. The curvature and shape of the longitudinal member 130 should be configured to correspond to the shape of the maxilla 14.

As shown in FIG. 3B, the longitudinal plate member 130 further includes a reference hole 174 that extends through the plate member 130 proximate to the central juncture 154 from the outer surface to the bone engaging surface. The osteotomy guiding implant 110 may initially be fastened to the maxilla 14 by inserting a fixation element through the reference hole 174 and into the maxilla 14. The fixation element inserted into the reference hole 174 may be temporary and is utilized while a surgeon correctly aligns the implant 110 so that an osteotomy guide may be created.

As shown in FIGS. 3A-3D, the longitudinal plate member 130 defines a plurality of apertures or holes 176. As best shown in FIG. 3B, the embodiment illustrated includes three holes 176 in each portion 146 and 150. The holes 176 are spaced apart and provide a template for the surgeon to drill pre-holes into the maxilla 14 that will align with the holes 58 defined by the longitudinal member 30 of the bone implant 10. Therefore, the surgeon will know where to secure the bone implant 10 to the first part 18 of the maxilla 14 after the osteotomy is performed by aligning the holes 58 of the bone implant 10 with the pre-drilled holes. Though it should be understood that in some cases, the longitudinal plate member 130 does not have the apertures 176, and thus the pre-drilled holes are not required to properly align the bone implant 10.

As shown in FIGS. 3A-3D, the osteotomy guiding implant's fingers 134 extend up from the upper edge 138 of the longitudinal member 130. In particular, two fingers 134 extend from each of the first and second portions 146, and 150 of the longitudinal member 130. However, it should be understood that any number of fingers 134 may extend up from the first and second portions 146, and 150.

As best shown in FIG. 3B, the fingers 134 are spaced apart along the longitudinal member 130 and extend substantially perpendicularly relative to the point on the longitudinal member 130 from where they extend. That is, the longitudinal member 130 is non-linear and will define tangents at different points along its edge 138. Therefore, the fingers 134 extend perpendicular with respect to a tangent taken at the point on the edge 138 from which the finger 134 extends. Though it should be understood that the fingers 134 do not have to extend perpendicularly and may extend at an angle relative to the longitudinal member 130.

As shown in FIG. 3B, each finger 134 of the osteotomy guiding implant 110 defines an aperture or hole 180. The holes 180 are configured to receive a drill bit so that guide holes may be drilled into the maxilla 14 to thereby define a guide path along which the osteotomy may be performed. As shown, the holes 180 of the fingers 134 will be positioned such that the guide path along which the osteotomy will be performed is appropriately located so that the bone fixation implant 10 may securely hold the first part 18 of the maxilla 14 relative to the second part 22. That is, the osteotomy will be located such that the fingers 80 of the bone implant 10 will be long enough to extend across the osteotomy to securely hold the first part 18 of the maxilla relative to the second part 22.

The osteotomy guiding implant 110, and in particular the longitudinal member 130 and the fingers 134, is pre-shaped to correspond to the pre-operative shape, and relative position of the first part 18 and the second part 22 of the maxilla 14. As best shown in FIG. 3C, the longitudinal member 130 and the fingers 134 include several non-linear undulations 190 that correspond to particular portions of the first part 18 and the second part 22 of the maxilla 14.

Figure 4:
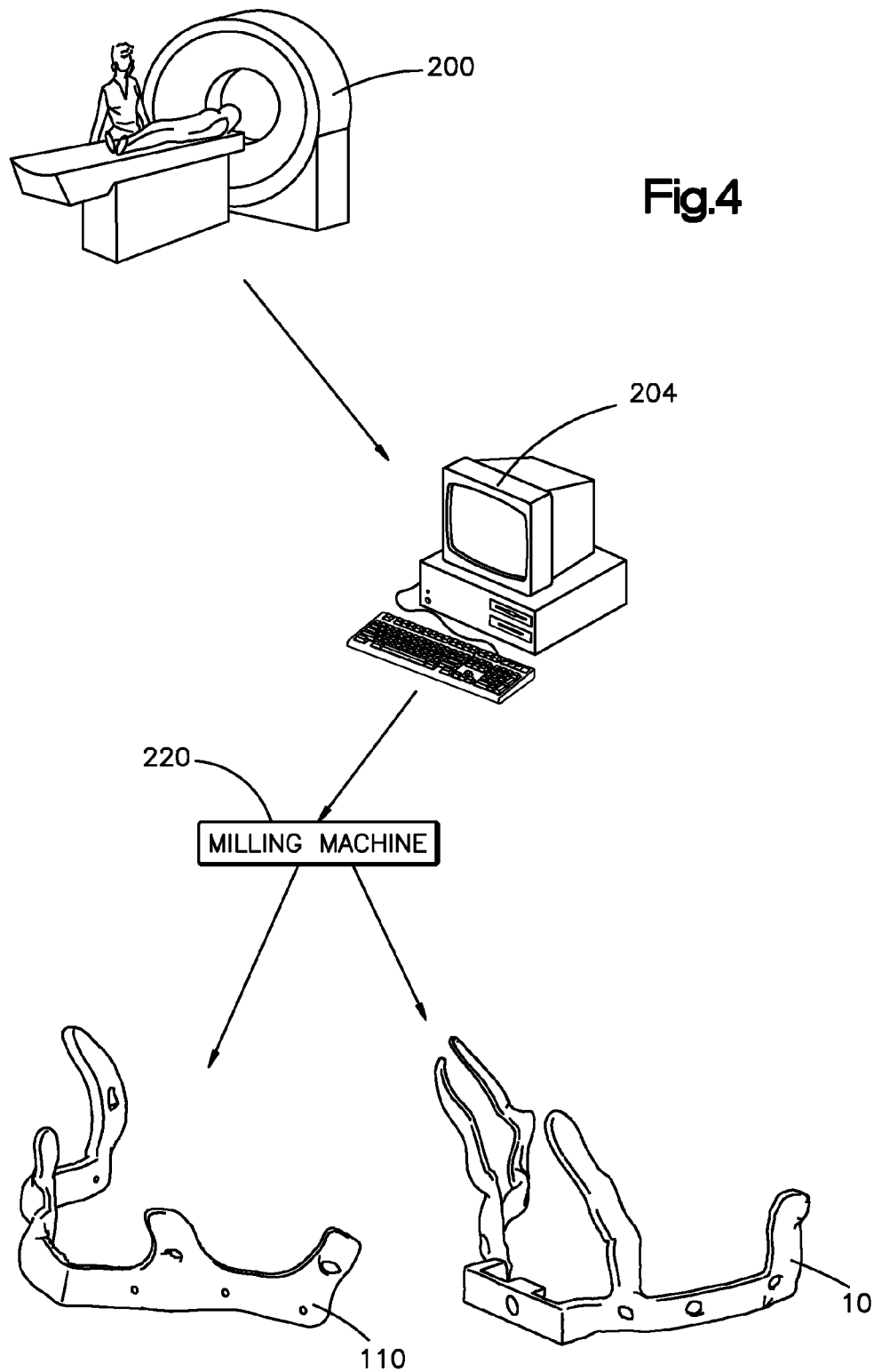
FIG. 4 is a diagram showing the process for customizing the bone fixation implant of FIGS. 2A-2D and the osteotomy guiding implant of FIGS. 3A-3D to correspond to an individual patient's maxilla.

Reference to FIG. 4, both the bone fixation implant 10 and the osteotomy guiding implant 110 are manufactured and shaped pre-operatively. Prior to the orthognathic surgery being performed, a 3-D image of the patient's skull, and in particular the patient's maxilla, such as maxilla 14 is obtained. This may be completed with a CT scanning device 200 or the like, with slices smaller than 1 mm preferred, and optimally between 0.2-1 mm. A high resolution for the slices is preferred, since the exact shape of the maxilla 14 should be determined from the CT scan slices. It will be appreciated that other scanning devices 200 besides a CT scanning device may be used so long as they provide three dimensional data corresponding to the shape of the maxilla 14.

Once the 3-D image of the patient's skull/maxilla is obtained, the image is loaded into a computer 204 to create a virtual model of the skull for manipulation by a user such as the surgeon. The computer 204 may be local (same general area as the CT scanning device 200) or remote where the image must be sent via a network. Similarly, the image loaded onto the computer 204 may be manipulated by a user that is working locally or remotely. Typically, however, the image is manipulated remotely by the surgeon who will be performing the orthognathic surgery.

The virtual model of the skull may be manipulated by the surgeon using standard software typical in the art. For example, Mimics, a software commercially available from Materialise, having a place of business in Leuven Belgium, may be used to process and manipulate the virtual model obtained from the CT scanning device 200. The software allows the surgeon to analyze the patient's maxilla and pre-operatively plan the patient's orthognathic surgery including the shape and design of the bone fixation implant a and an osteotomy guiding implant.

Using the virtual model of the patient's skull/maxilla, the surgeon may first make a virtual model of an osteotomy guiding implant, such as the osteotomy guiding implant 110 shown in FIGS. 3A-3D. This is accomplished by determining on the virtual model of the skull where the osteotomy is to be performed, and then actually performing a virtual osteotomy on the virtual model. Once the virtual osteotomy is complete, the surgeon can begin making the virtual model of the osteotomy guiding implant 110. At this point, it should be understood that the virtual model of the skull and in particular the maxilla still has its pre-operative shape and position. Therefore, the longitudinal plate member 130 and the fingers 134 of the osteotomy guiding implant 110 that is being made will correspond to the pre-operative shape of the patient's maxilla. The holes 180 that are formed in the fingers 134 of the osteotomy guiding implant 110 will be made in the virtual model to correspond to the virtual osteotomy that was performed on the virtual model of the skull. Therefore, the osteotomy guiding implant 110 manufactured using the virtual model, will define holes 180 that create a guide path for the surgeon to follow while performing the osteotomy. In this way, the actual osteotomy performed on the patient will match the virtual osteotomy that was performed on the virtual model.

After the virtual model of the osteotomy guiding implant 110 is complete, the surgeon or other operator may manipulate the first part 18 (the cut off portion) of the virtual model of the maxilla 14 from a first undesired position to a second desired position. Once the first part 18 is positioned and the virtual model portrays the post-operative shape and position of the patient's maxilla, as approved by the surgeon, a virtual model of a bone fixation implant, such as the bone fixation implant 10 shown in FIGS. 2A-2D, can be made. At this point, it should be understood that the virtual model of the skull and in particular the maxilla has a post-operative shape and position. Therefore, the longitudinal plate member 30 and the fingers 80 of the bone fixation implant 10 that is being made will correspond to the post-operative shape of the patient's maxilla.

The virtual models of the osteotomy guiding implant 110 and the bone fixation implant 10 may be downloaded or transferred from the computer 204 to a CAD/CAM milling machine 220 or the like. The milling machine 220 will machine the osteotomy guiding implant 110 and the bone fixation implant 10 out of any desired material. Once the osteotomy guiding implant 110 and the bone fixation implant 10 have been manufactured, the surgeon may begin the orthognathic surgery on the patient.

Figure 5A:
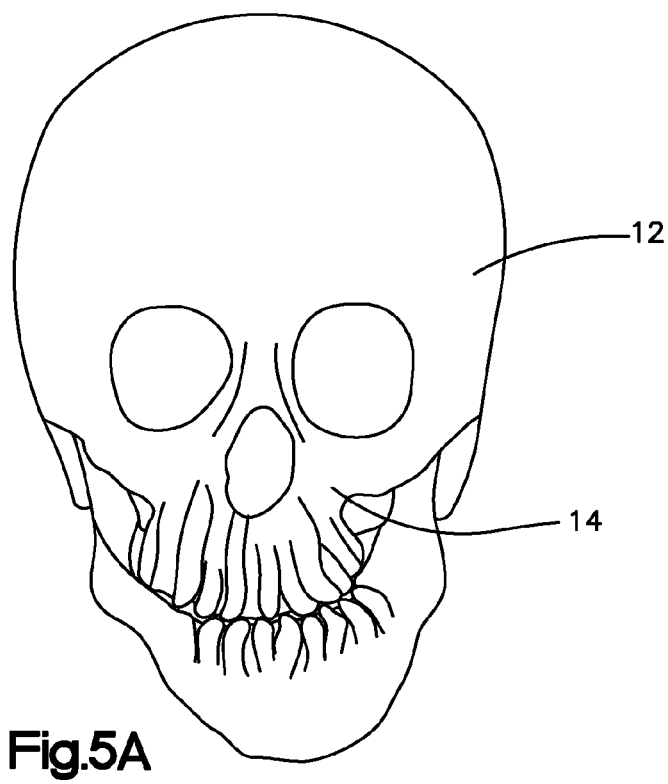
Figure 5B:
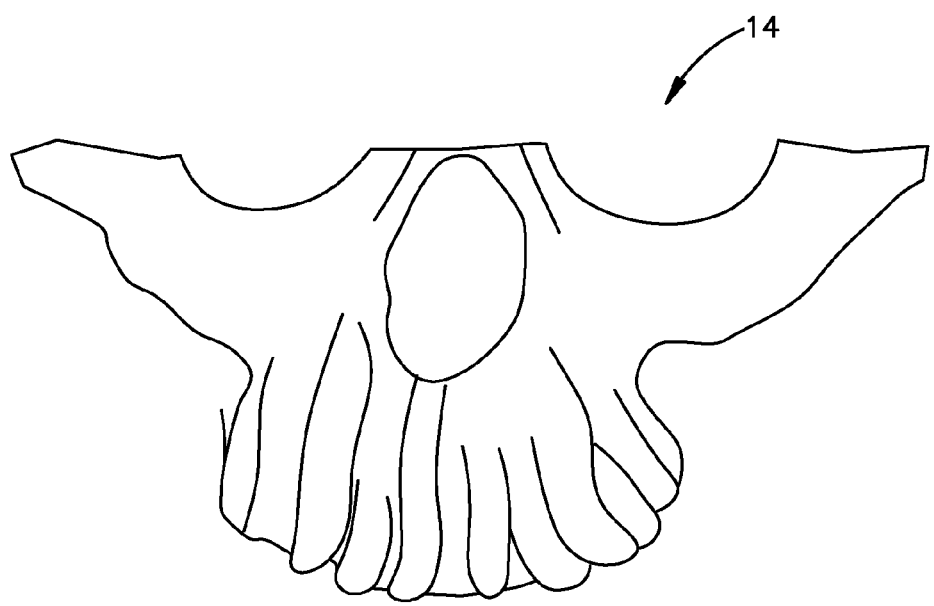
FIG. 5B is an enlarged detailed view showing the pre-operative shape of the maxilla of the skull shown in FIG. 5A.

FIGS. 5A-5J show an example method of performing an orthognathic surgery using the osteotomy guiding implant 110 and the bone fixation implant 10. It should be understood that prior to the surgery, the osteotomy guiding implant 110 and the bone fixation implant 10 are pre-shaped to substantially correspond to the individual patient's maxilla. FIG. 5A shows an example skull 12 having a maxilla 14 that needs to be repositioned. FIG. 5B is a detailed view of the maxilla 14 shown in FIG. 5A. As shown, the maxilla 14 at this point has a pre-operative shape. An osteotomy is to be performed on the maxilla 14 to thereby separate the maxilla 14 into a first part 18 and a second part 22, so that the first part 18 can be repositioned, as will be described below.

Figure 5C:
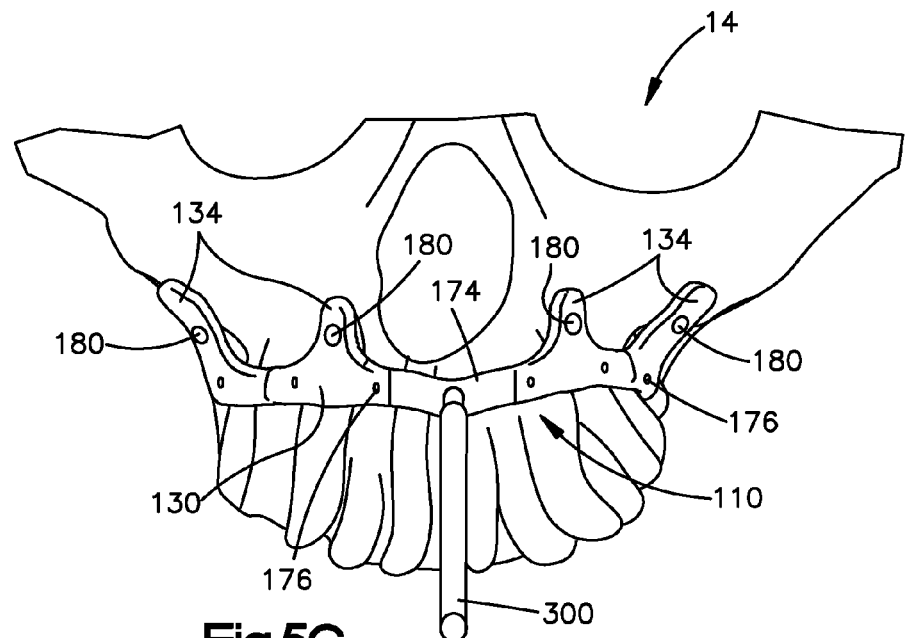
FIG. 5C is a front view of the maxilla shown in FIG. 5B, showing the osteotomy guiding implant of FIGS. 3A-3D being attached to the maxilla.

As shown in FIG. 5C, the osteotomy guiding implant 110 may be placed onto the maxilla 14. As stated before, the osteotomy guiding implant 110 is pre-shaped to correspond to the pre-operative shape of the maxilla 14, and therefore will lie flush against the maxilla 14. In other words both the longitudinal plate member 130 and the fingers 134 will be pre-shaped to correspond to the pre-operative shape of the maxilla 14. Once properly positioned, the osteotomy guiding implant 110 may be temporarily affixed to the maxilla 14 by inserting a screw 300 into the reference hole 174 of the osteotomy guiding implant 110 and screwing it into the maxilla 14 with a driver 300.

Figure 5D:
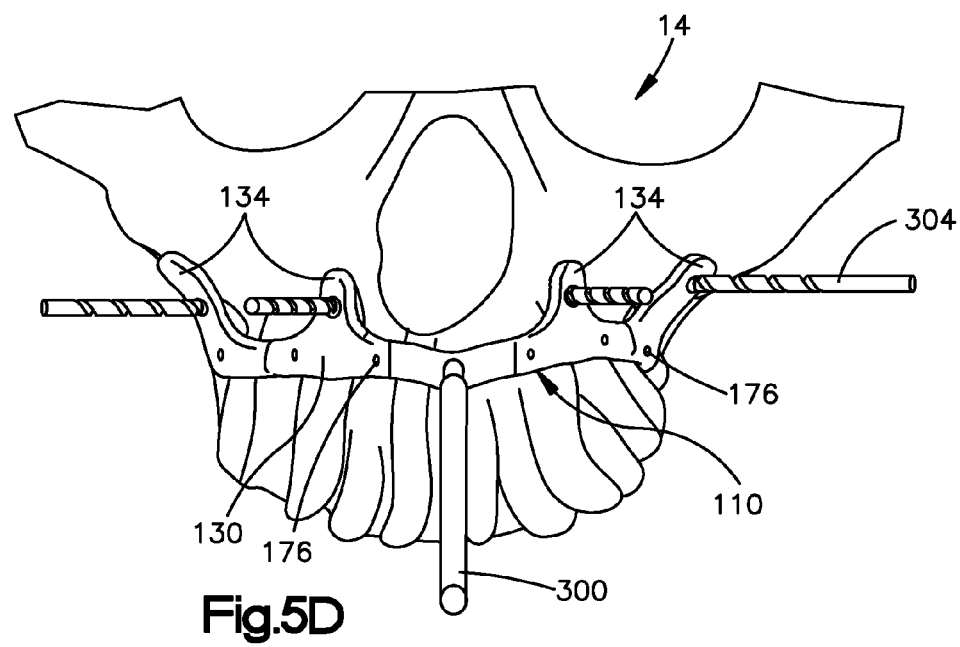
FIG. 5D is a front view of the of the maxilla shown in FIG. 5C, showing holes being drilled into the maxilla through guide holes defined by the osteotomy guiding implant.
Figure 5E:
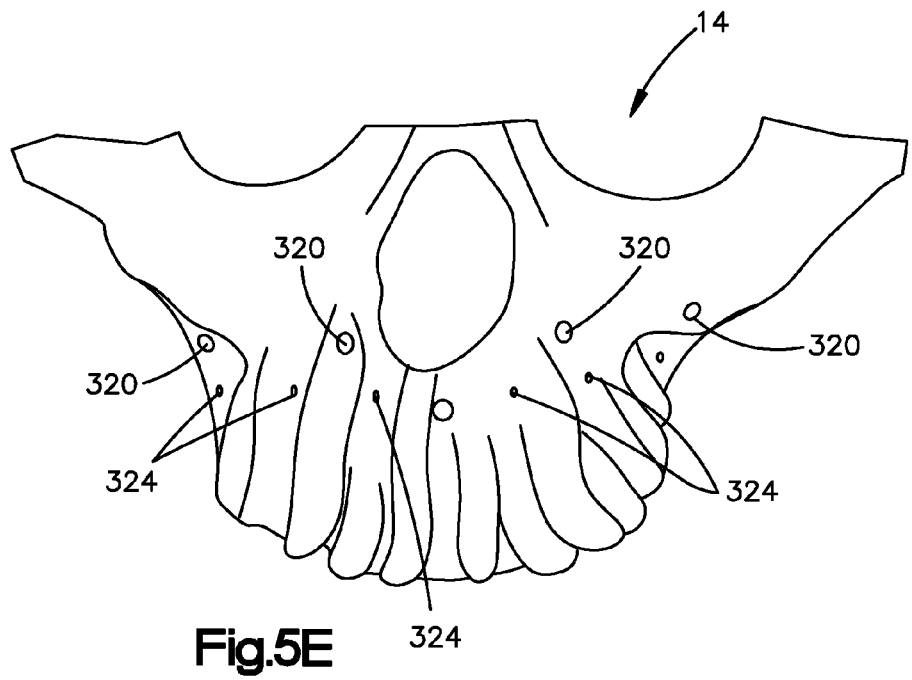
FIG. 5E is a front view of the maxilla shown in FIG. 5D, showing the drilled holes.

As shown in FIG. 5D, the surgeon may then drill holes into the maxilla 14 using a drill bit 304. As shown, the drill bit 304 may be inserted into the holes 180 defined by the fingers 134 of the osteotomy guiding implant 110. As stated before, the holes 180 are pre-planned and positioned so that the surgeon can create a cutting path for the surgeon to follow while performing the osteotomy. For example, as shown in FIG. 5E, four holes 320 are drilled into maxilla 14 using the osteotomy guiding implant 110. While four holes 320 are shown, it should be understood that the osteotomy guiding implant 110 may be configured so that any number of holes 320 may be made using the osteotomy guiding implant 110. For example, the osteotomy guiding implant 110 may be made to have six fingers 134 so that six holes 320 may be made in the maxilla.

As shown in FIG. 5D, drill bit 304 or another drill bit may be inserted into holes 176 defined by the longitudinal member 130 of the osteotomy guiding implant 110. As shown in FIG. 5E, six holes 324 are drilled into the maxilla 14 using the osteotomy guiding implant 110. While six holes 324 are shown, it should be understood that the osteotomy guiding implant 110 may be configured so that any number of holes 324 may be made using the osteotomy guiding implant 110. The holes 324 will act as a guide for the surgeon to properly place the bone implant 10 to the maxilla. To ensure that bone implant 10 will be securely affixed to the maxilla 14, the holes 324 are smaller than the holes 58 defined by the bone implant 10. Thus when a screw is affixed the threads of the screw will grab a portion of the bone.

Figure 5F:
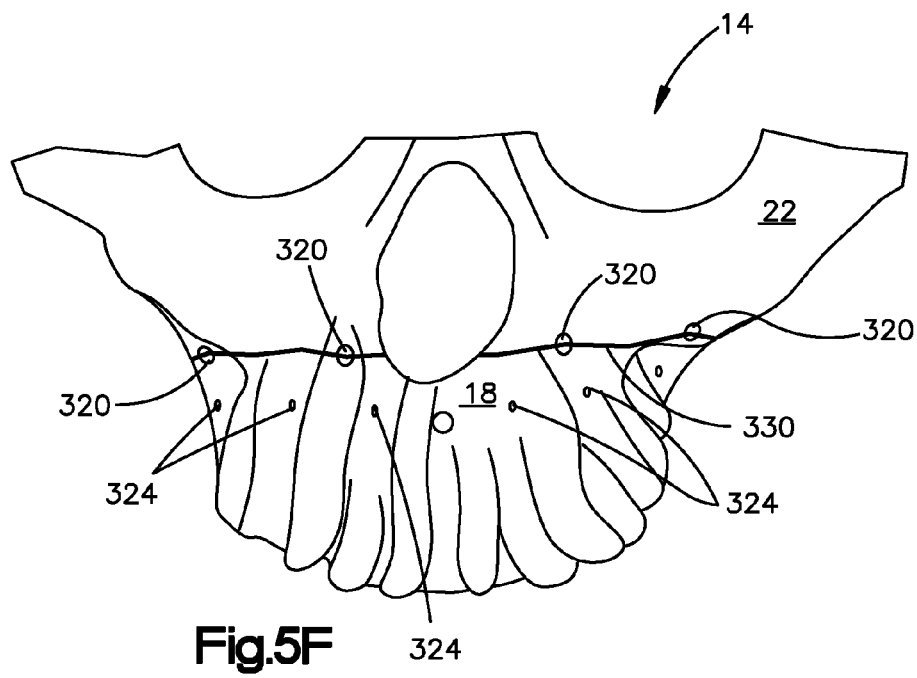
FIG. 5F is a front view of the maxilla shown in FIG. 5E, showing the osteotomy performed on the maxilla, using the holes as a cutting guide.
Figure 5G:
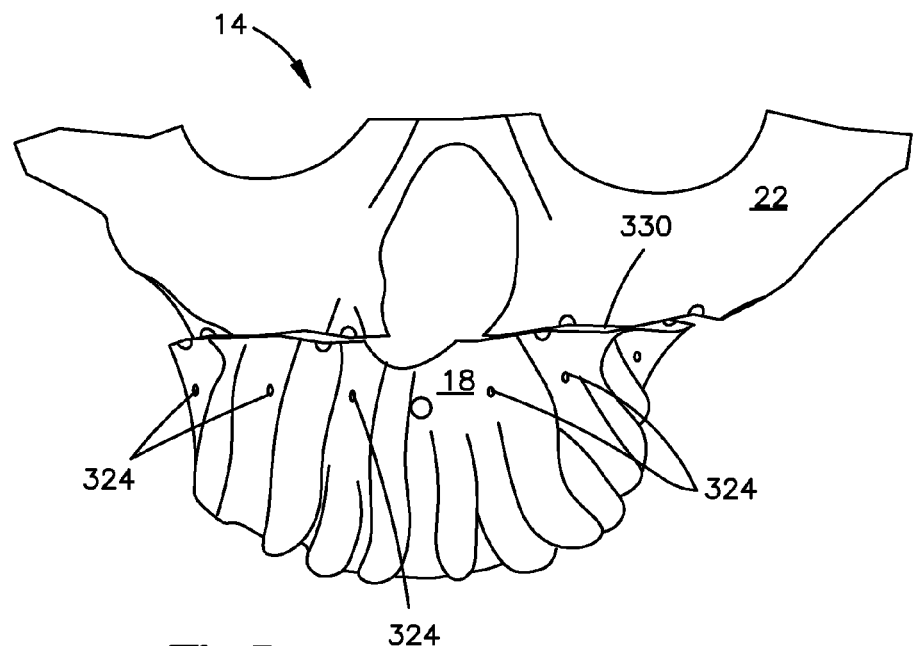
FIG. 5G is a front view of the maxilla shown in FIG. 5F, showing a segmented portion of the maxilla being repositioned into a post-operative shape.

As shown in FIG. 5F, the osteotomy guiding implant 110 may be removed and the surgeon may perform an osteotomy 330 on the maxilla 14 along the cutting path created by the holes 320. In the embodiment illustrated, the cutting path extends from one hole 320 to an adjacent hole 320 until the osteotomy is complete. As shown in FIG. 5G, the osteotomy 330 separates the maxilla into a first part 18 and a second part 22. While the second part 22 remains intact with the skull, the first part 18 is free to be repositioned by the surgeon, for example as shown in FIG. 5G.

Once the first part 18 of the maxilla 14 is repositioned, the bone fixation implant 10 may be placed onto the maxilla 14. As stated before, the bone fixation implant 10 is pre-shaped to correspond to the post-operative shape of the maxilla 14, and therefore will lie flush against the maxilla 14 even after the first part 18 of the maxilla 14 has been repositioned. In other words both the longitudinal plate member 30 and the fingers 80 of the bone plate 10 will be pre-shaped to correspond to the post-operative shape of the maxilla 14. Once properly positioned, the bone fixation implant 10 may be temporarily affixed to the maxilla 14 by inserting a screw into the reference hole 74 of the bone fixation implant 10 and screwing it into the maxilla 14 with the driver 300. In most cases the reference hole 74 of the bone fixation implant 10 will line up with the hole created in the maxilla 14 by the screw that was used to temporarily affix the osteotomy guiding implant 110 to the maxilla 14.

Figure 5H:
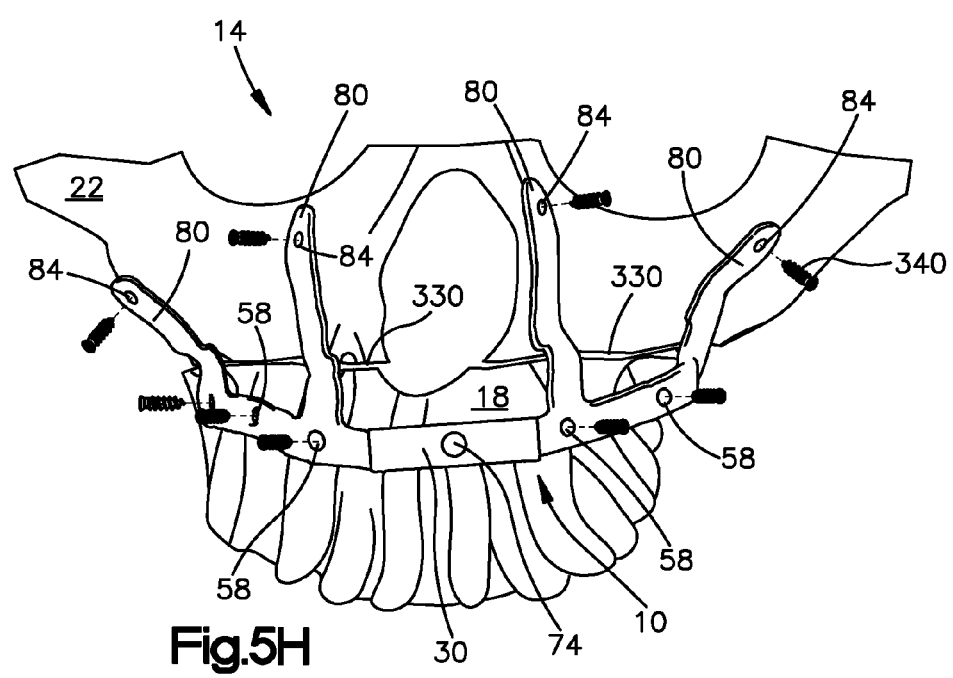
FIG. 5H is a front view of the maxilla shown in FIG. 5G, showing the bone fixation implant of FIGS. 2A-2D being attached to the maxilla.
Figure 5I:
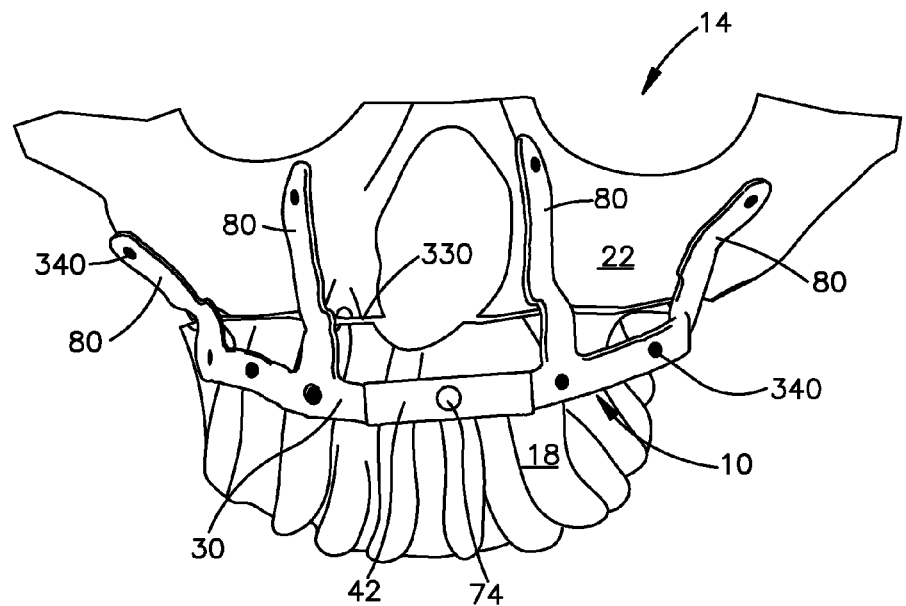
FIG. 5I is a front view of the maxilla shown in FIG. 5H, showing the bone fixation implant attached to the maxilla.

As shown in FIGS. 5H and 5I, a plurality of screws 340 may be inserted into the holes 58 and the holes 84 of the bone fixation implant 10. As shown, the fingers 80 of the bone fixation implant 10 are affixed to the second part 22 of the maxilla 14 with the screws 340, and the longitudinal member 30 of the bone fixation implant 10 is affixed to the first part 18 of the maxilla 14 with the screws 340. Therefore, the bone fixation implant 10 is affixed to the maxilla 14 on either side of the osteotomy 330.

Figure 5J:
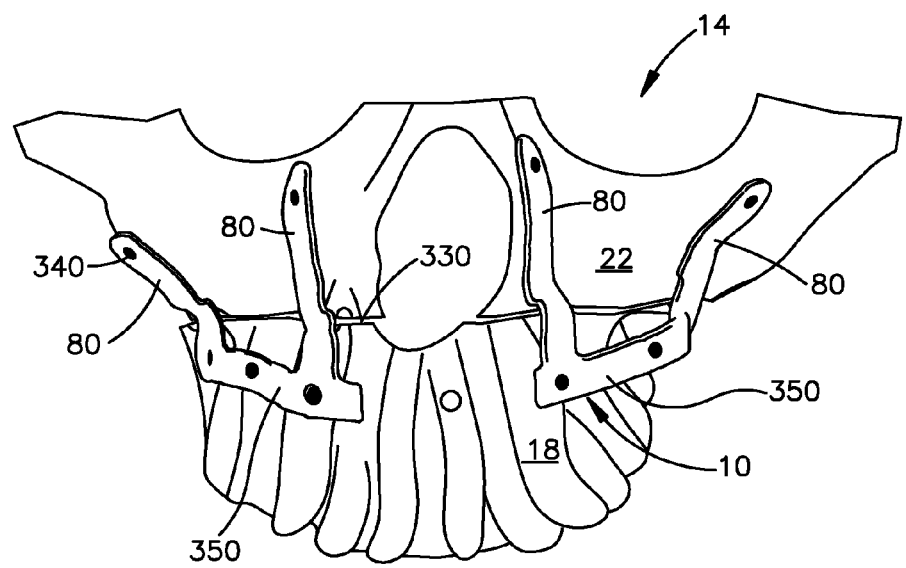
FIG. 5J is a front view of the maxilla shown in FIG. 5I, showing a bridge portion of the bone fixation implant removed.

As shown in FIG. 5J, the bridge member 42 may then be removed from the bone fixation implant 10 thereby separating the bone fixation implant 10 into two separate parts 350. In this way, the bone fixation implant 10 may be considered to be a single bone fixation implant 10 that is configured to be separated into two separate implant segments or sections after the bone fixation implant 10 has been affixed to bone. As stated before, the bridge member 42 may be removed by either snapping it away or by using pliers or snips to cut the bridge member away at the junctions 54. It should be understood, however, that the bridge member 42 may be removed using any method known in the art.

Once the bridge member 42 is removed, the bone fixation implant 10 is completely installed. Therefore, the surgery may be completed, and the implant 10 may either remain within in the patient or be removed at a later time.

It should be understood that the bone fixation implant 10 and the osteotomy guiding implant 110 may be sold separately or as a kit. It should be understood, however, that the osteotomy guiding implant 110 and bone fixation implant 10 may be manufactured and delivered at different times even though they are part of the same kit. The kit may also include all of the fixation elements required to affix the bone fixation implant 10 to the maxilla 14 as well as any tools required to complete the procedure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description. For example, while the bone fixation implant 10 is shown as having a removable bridge member 42, it should be understood that the bone fixation implant may remain intact after it has been installed. In other words, the longitudinal member 30 of the bone fixation implant 10 may be a single continuous plate that is configured to remain a single piece after installation of the bone plate 10. Furthermore, while the holes 180 of the osteotomy guiding implant 110 are positioned in the fingers 134 of the implant 110 such that a guide path is created for the osteotomy to be performed along the holes, the holes 180 may be positioned to create an alternative guide. For example, the holes 180 may be positioned to create holes in the maxilla 14 that line up with the holes 58 defined by the longitudinal member 30 of the bone fixation implant 10. In such a case the osteotomy would be performed above the holes 180. Furthermore, while the bone fixation implant 10 and the osteotomy guiding implant 110 have been described for use in orthognathic surgeries involving the maxilla, it should be understood that the bone fixation implant 10 and the osteotomy guiding implant 110 may be used in orthognathic surgeries involving the mandible. Additionally, the bone fixation implant 10 and the osteotomy guiding implant 110, and the described concepts are not limited to orthognathic surgeries and may be utilized in surgeries for other parts of the body that may need to affix a first segmented portion of bone relative to a second integral portion of bone.

What is claimed is:

1. A method of customizing a pre-shaped implant for use in orthognathic surgery of a maxilla, the method comprising:
   obtaining a pre-operative 3-D model of a patient's maxilla in a computer, whereby a first portion of the maxilla and a second portion of the maxilla define a first relative position;
   manipulating the pre-operative 3-D model of the maxilla into a planned post-operative shape whereby the first portion of the maxilla and the second portion of the maxilla define a second relative position that is different than the first relative position; and
   custom constructing a virtual model of a bone fixation implant to match the planned post-operative shape of the maxilla, the bone fixation implant including a plate member pre-shaped to attach to the first portion of the maxilla, and at least one finger extending from the plate member shaped to attach to the second portion of the maxilla.

2. The method of claim 1, wherein the bone fixation implant is constructed from Titanium.

3. The method of claim 1, further comprising the step of custom constructing a guiding implant to match the pre-operative shape of the patient's maxilla, the guiding implant including a plate member defining a plurality of apertures, the apertures being arranged to provide a template for pre-osteotomy drilling of holes in the maxilla.

4. The method of claim 3, wherein the step of custom constructing the guiding implant is performed prior to the step custom constructing the bone fixation implant.

5. The method of claim 1, wherein the obtaining step further comprises scanning the patient's maxilla with a 3-D scanning device.

6. The method of claim 5, wherein the 3-D scanning device is a CT scanning device.

7. The method of claim 6, wherein the obtaining step further comprises obtaining raw data of the maxilla in slices of less than 1 mm each, the raw data being arranged to collectively form the 3-D model of the maxilla.

8. The method of claim 7, wherein the obtaining step further comprising obtaining the raw data of the maxilla in slices greater than 0.2 mm.

9. The method of claim 1, further comprising the step of analyzing the 3-D model of the maxilla to determine a cut line for a virtual osteotomy procedure, wherein the analyzing step is performed prior to the manipulating step.

10. The method of claim 9, wherein the analyzing step further comprises the step of performing a virtual osteotomy on the 3-D model of the maxilla at the cut line.

11. The method of claim 10, wherein the analyzing step further comprises the step of custom constructing a virtual model of a guiding implant to match the pre-operative shape of the patient's maxilla, the guiding implant including a plate member defining a plurality of apertures that are aligned along the cut line.

12. The method of claim 11, further comprising the step of transferring the virtual model of the guiding implant and the virtual model of the bone fixation implant to a machine that is configured to produce the guiding implant and the bone fixation implant.

13. The method of claim 12, wherein the transferring step further comprises transferring the virtual models to a milling machine.

14. The method of claim 13, further comprising the step of milling the guiding implant from the virtual model of the guiding implant.

15. The method of claim 1, further comprising the step of milling the bone fixation implant from the virtual model of the bone fixation implant.

16. The method of claim 1, further comprising the step of performing a virtual osteotomy on the 3-D model of the maxilla prior to the manipulating step.

17. The method of claim 1, further comprising the step of milling bone fixation implant from the virtual model of the bone fixation implant.

* * * * *